(12) United States Patent
Pan

(10) Patent No.: US 10,393,655 B2
(45) Date of Patent: Aug. 27, 2019

(54) APPARATUS FOR RETRO-REFLECTION MEASUREMENT USING A HOLED MIRROR AND CIRCULAR APERTURE FOR ANNULAR BAND DETECTION

(71) Applicant: EVERFINE PHOTO-E-INFORMATION CO., LTD., Hangzhou, Zhejiang Province (CN)

(72) Inventor: Jiangen Pan, Hangzhou (CN)

(73) Assignee: EVERFINE PHOTO-E-INFORMATION CO., LTD. (CN)

( * ) Notice: Subject to any disclaimer, the term of this patent is extended or adjusted under 35 U.S.C. 154(b) by 0 days.

(21) Appl. No.: 15/529,464

(22) PCT Filed: Apr. 8, 2015

(86) PCT No.: PCT/CN2015/076082
§ 371 (c)(1),
(2) Date: May 24, 2017

(87) PCT Pub. No.: WO2016/082416
PCT Pub. Date: Jun. 2, 2016

(65) Prior Publication Data
US 2017/0261429 A1 Sep. 14, 2017

(30) Foreign Application Priority Data

Nov. 24, 2014 (CN) .......................... 2014 1 0679212
Nov. 24, 2014 (CN) ..................... 2014 2 0711898 U

(51) Int. Cl.
*G01N 21/55* (2014.01)

(52) U.S. Cl.
CPC ....... *G01N 21/55* (2013.01); *G01N 2021/551* (2013.01); *G01N 2201/065* (2013.01);
(Continued)

(58) Field of Classification Search
CPC ............. G01N 2021/551; G01N 21/55; G01N 2201/065; G01N 2201/0627; G01N 2201/0636
See application file for complete search history.

(56) References Cited

U.S. PATENT DOCUMENTS 3,771,880 A * 11/1973 Bennett ................... G01N 21/55
356/446
4,062,623 A * 12/1977 Suzuki ...................... G03F 9/70
356/401
(Continued)

*Primary Examiner* — Michael P LaPage
(74) *Attorney, Agent, or Firm* — PROI Intellectual Property US

(57) ABSTRACT

This invention relates to an apparatus for retro-reflection measurement. By using the one or more sampling devices each consists of a holed mirror and an circular aperture, and corresponding one or more measuring devices, it realize the retro-reflection measurement in one or more observation angles at one time. By flexibly selecting the size of the circular apertures and holed mirrors, it can accurately adjust the measuring annular bands and corresponding observation angles. Without any other intermediate devices, it can realize complete annular band of light measurement which ensures the measurement accuracy. At the same time, filters and monitor device can be set flexibly to realize various measurement functions. It has the advantages of speed measurement, high accuracy, small volume, wide application, comprehensive functions, and can be widely applied in laboratory, industrial production line and field measurement etc.

15 Claims, 4 Drawing Sheets

Figure 1:
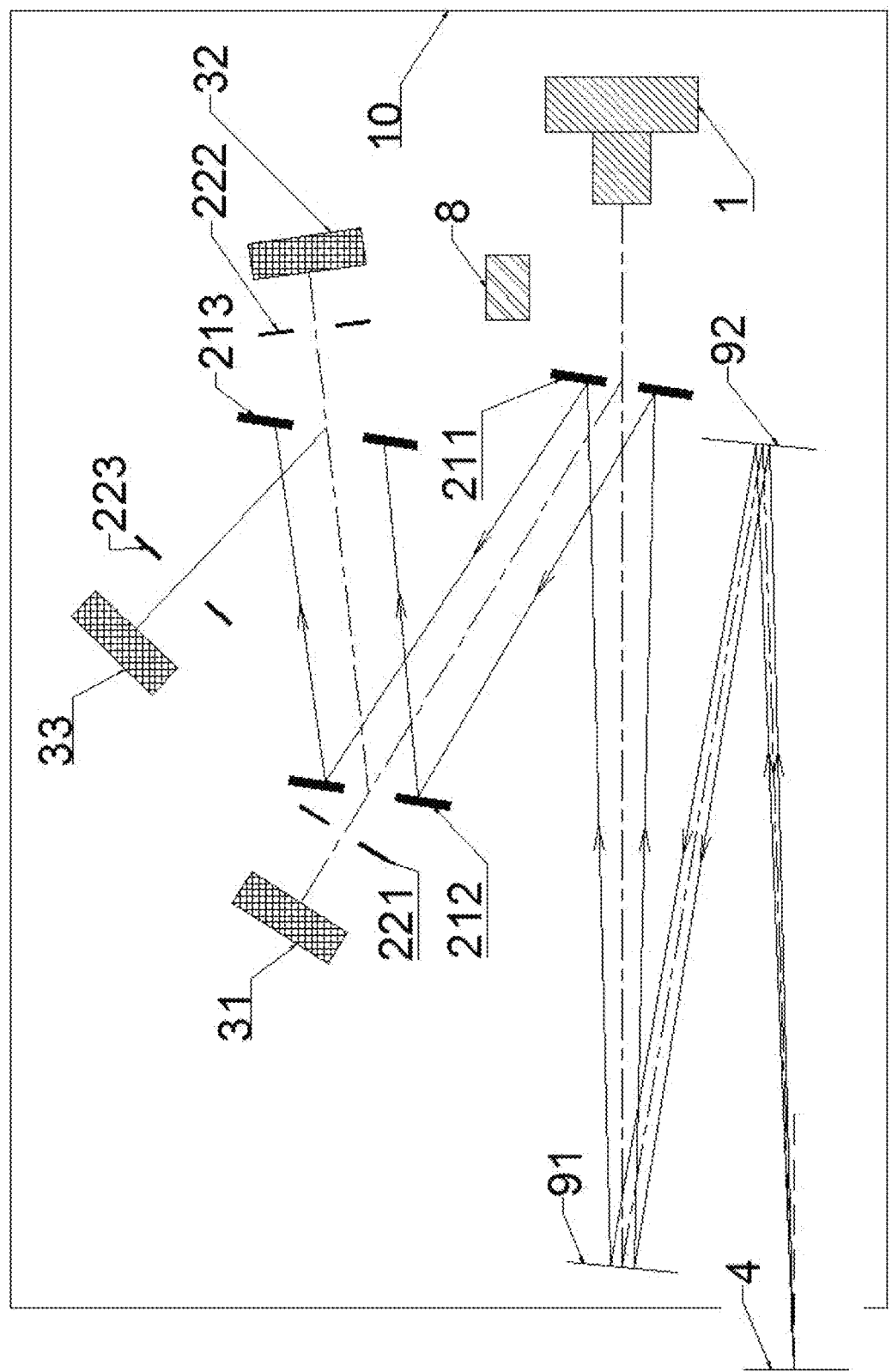

(52) U.S. Cl.
 CPC ........... *G01N 2201/0627* (2013.01); *G01N 2201/0636* (2013.01)

(56) References Cited

U.S. PATENT DOCUMENTS

| | | | | |
|---|---|---|---|---|
| 4,368,982 | A * | 1/1983 | Van Arnam | G01N 21/55 250/224 |
| 4,831,276 | A * | 5/1989 | Hyakumura | G01N 21/55 250/225 |
| 7,961,328 | B2 * | 6/2011 | Austin | G01N 21/55 356/445 |
| 2002/0111546 | A1 * | 8/2002 | Cook | A61B 5/0059 600/322 |
| 2012/0287432 | A1 * | 11/2012 | Eckhardt | G01J 3/42 356/326 |

* cited by examiner

APPARATUS FOR RETRO-REFLECTION MEASUREMENT USING A HOLED MIRROR AND CIRCULAR APERTURE FOR ANNULAR BAND DETECTION

TECHNICAL FIELD

This disclosure relates to an optical radiation measurement, and more particularly relates to an apparatus for retro-reflection measurement.

BACKGROUND

Retro-reflective material is mainly used for traffic signs, marking, sight guidance line and other traffic safety warning signs. It plays an important role in the protection of traffic safety, and retro-reflection characteristic is the most effective and direct method to evaluate this material. The retro-reflection measurement requires very small observation angle which is the angle between the retroreflector axis and the observation axis, therefore a long distance is often needed to precisely control the angle, moreover, the measurement is usually completed in a large dark room, which greatly limits its application in practical engineering measurement. For industrial production line and on-site rapid measurement, an annular band optical path is adopted to shorten the distance and meet the illumination/observation condition for retro-reflection measurement.

The U.S. Pat. No. 7,961,328 B2 disclosed a system and method for measuring the photometric retroreflectivity of materials. By the combination of an annular transparent portion and an annular mirrored portion, it defines two annular beams that realize the measurement in two observation angles. However, multiple support devices are needed to support the annular transparent portion and the annular mirrored portion, which can cause the incomplete of annular beam and affect measurement accuracy; furthermore, it increases the risk of instability of the mechanism system. The annular transparent portion also requires small size of beam splitter mirror which will produce larger energy loss, and will also introduce the measuring error and refraction process. Besides, the mall size mirror is difficult to be processed and fixed.

SUMMARY

To overcome the disadvantages of existing technology, this invention provides a speed, accurate, wide applicable and portable retro-reflection measurement device. The retro-reflection characteristics in multi different observation angles can be obtained by only one time sampling.

This invention can be realized by the following technical schemes: an apparatus for retro-reflection measurement, comprising: a light source, one or more sets of sampling devices for annular measurement, and one or more measurement devices corresponding to the sampling devices; one set of sampling device consists of a holed mirror and an circular aperture; the illumination light path is the light from the said light source goes to the test sample in a certain entrance angle, and the observation light path is the retro-reflect light from the test sample passes through the holed mirror and the circular aperture to form a annular band which meets the observation angle condition and is then received by the corresponding measurement device.

In this invention, the light emitted by the light source irradiates to the test sample, the sampling device is set in front of the measuring device. Each set of sampling device consists of a holed mirror and a circular aperture of a certain size to define a annular band of light in a specified observation angle, therefore the measurement device receives the annular band of retro-reflection light from test sample. Multi sampling devices can shape different sizes of measuring annular bands, and the retro-reflection light is measured in different observation angles. Compared to the existing technologies, this invention provides a novel retro-reflection method which introduces sampling device consists of a circular aperture and a holed mirror. The optical path is designed simply, artfully and needs no support device. It can obtain the complete signal in a specified annular band and has the advantages of high accuracy and stability.

The invention also can be further defined and improved by the following technical proposal:

In a sampling device, the diameter of the open hole in the holed mirror is less than the diameter of the circular aperture, and the combination of the holed mirror and the circular aperture shape an annular band of light that the holed mirror reflects the light outer the inner diameter while the circular aperture cuts the light outer the external diameter of the annular band. One sampling device defines an observation angle. For example, it need to measure the annular band of light in the angle of $(\alpha \pm \Delta\alpha)$ for the observation angle $\alpha$, the size of the hole in the holed mirror corresponds to $(\alpha - \Delta\alpha)$, the reflection beam angle is greater than $(\alpha - \Delta\alpha)$. The diameter of the circular aperture corresponds to $(\alpha + \Delta\alpha)$, only the light with angle less than $(\alpha + \Delta\alpha)$ can through the aperture. Combining the holed mirror and circular aperture, the measuring device receives annular band of light in the range of $(\alpha - \Delta\alpha) \sim (\alpha + \Delta\alpha)$.

The center of the holed mirror and the center of the circular aperture located in the optical axis so as to ensure the accuracy of observation angle. Otherwise, the holed mirror and the circular aperture may shape an irregular area of light that can't meet the demands of measurement.

As a technical scheme, it comprises two or more sampling devices; along the observation light path, the holed mirror of the rear sampling device is in front of the circular aperture of the front sampling device. Take two observation angles of $\theta$ and $\varphi$ ($\theta < \varphi$) as an example, the light retro-reflected light incident into the holed mirror in the sampling device for observation angle $\theta$, which reflects the light beam larger than $(\theta - \Delta\theta)$ to the other holed mirror in the sampling device for observation angle $\varphi$; and the light beam less than $(\varphi - \Delta\varphi)$ pass through the hole, and the circular aperture in the sampling device observation angle $\theta$ set behind to cut off light beam great than $(\theta + \Delta\theta)$, the shaped annular light band $(\theta \pm \Delta\theta)$ is then received by a following measuring device. Meanwhile, the light beam greater than $(\varphi - \Delta\varphi)$ is reflected and then cut by the other circular aperture and is received by the other measuring device for observation angles $\varphi$ measurement.

The measuring annular bands shaped by the multi sets of sampling devices are sequentially arranged from small to large in the observation light path. Take measurement band ring with $\theta$ and $\varphi$ observation angle ($\theta < \varphi$) as an example, the sampling device for observation angle $\theta$ is located in front of that for observation angle $\varphi$. It can not only realize the retro-reflection measurement of multiple observation angles, but also can improve the efficiency of the optical path.

As preferred, the above observation angles of the annular bands are 0.2°, 0.33° or 0.5°, so as to meet practical measurement needs. It should be noted that, by flexibly choose the size of holed mirror and the circular aperture, this invention can realize other observation angles.

As a technical scheme, the invention further comprises one or more color filters set in the observation path and/or illumination path. The annular band light passes though the color filter and is then received by the measurement device, with different kind of filters, and corresponding measuring device, it can realize the quantities' measurement. For example, the color filter matching the measuring device to the CIE $V(\lambda)$ function, can realize photometric measurements. In addition, further comprises a color filter wheel in which the color filters are located and switched into the light path one by one.

Figure 3:
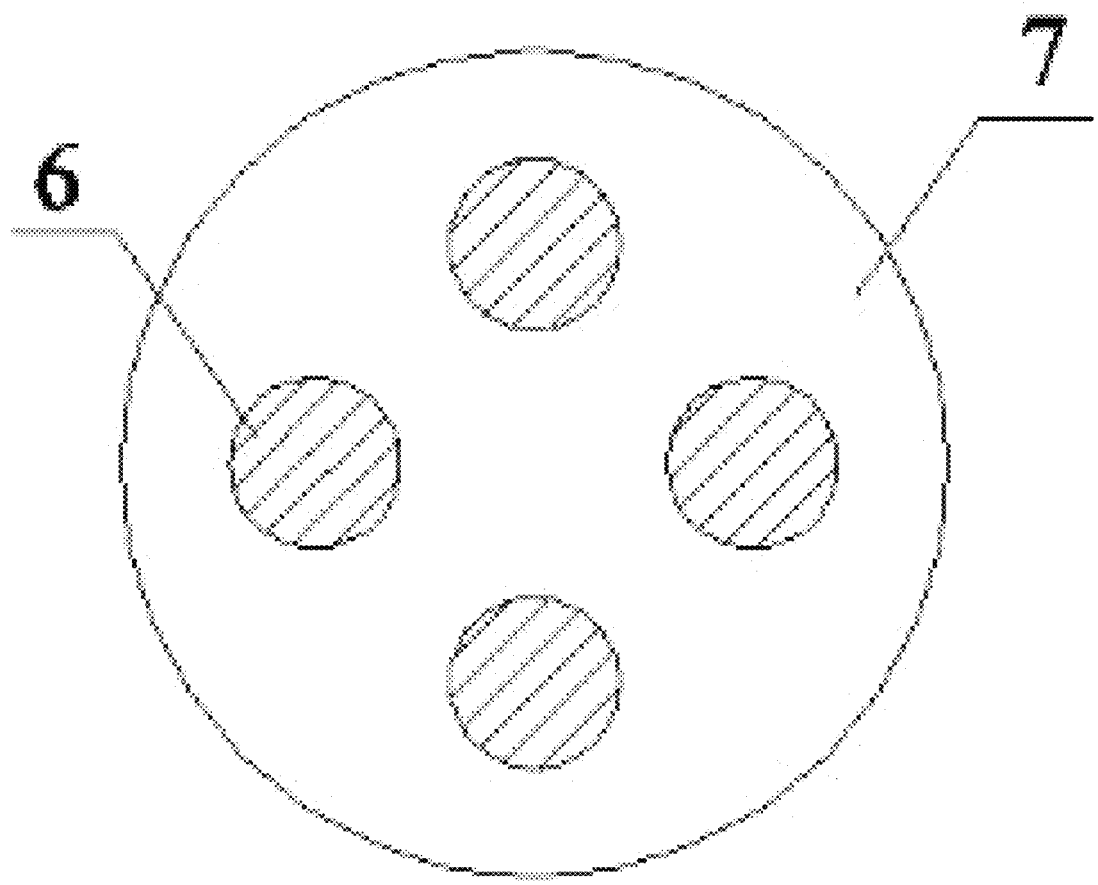

This invention comprises one or more sampling devices. When including a sampling device, the filter can be arranged in front of the measuring device at an arbitrary position in the observation path. When including multiple devices, the above observation path includes the common observation light path of the two or more measuring annular band and the independent observation light path corresponding to each individual measuring annular band. As shown in FIG. 3, light path A and B contain three measuring annular band optical signals and light path C includes latter two measurement band. The independent observation path of a former sampling device is behind the holed mirror of the rear sampling device.

The said color filters set in the common observation light path or independent observation light path. If the filter set in the common observation path, it realizes retro-reflect light measurement in multi observation angles. For example, in the A or B light path, setting a CIE $V(\lambda)$ matching filter, can realize the three annular band. If the above filter is arranged in the optical path of C, it can realize measurement of latter two annular bands. Filters can be the same or different. In addition, multiple filters can be set in a filter wheel to realize different retro-reflection measurement in a same observation angle. For example, the measuring device is a monochrome CCD, it can set three filters in the filter plate to matching the CIE tristimulus values $x(\lambda)$, $y(\lambda)$ and $z(\lambda)$; under the driving of the driving device, it can realize the tristimulus values' measurement.

As a technical scheme, the said light source comprises one or more programmable LEDs of different color; the said LEDs emit light independently or with combination, and the light goes to the test sample directly or indirectly. The light source in the invention can be achieved in a variety of ways, including LED array with a number of different color LED. Under the control of a programmable system, the light from the LEDs independently or with combination, and irradiate to the test sample. It can also include an integrating sphere, one or more LEDs emit light independently or with combination, and then mixed by integrating sphere, irradiate to the test sample. Due to the narrow beam angle of LED light, the uniformity of the light intensity of the light source can not be guaranteed. By using integrating sphere to mix the light and then irradiate to the test sample indirectly, it can ensure the light uniformity irradiated on the test sample, so as to avoid the measurement error due to the non-uniform of the illumination light. The drive mode of the LEDs can flexibly be selected, preferred by way of driving pulse, by phase-locked amplification technology, effectively remove stray light, improve the measurement accuracy, and subsequent signal processing is more simple, as to improve the efficiency of testing.

In addition, collimator, aperture or other optical devices can also be set in the light path. For example, a collimator is arranged on the light path after the light source and a aperture is set in the light path after the collimator. A color filter can be set in the illumination path for spectral correction of light source.

As a technical scheme, the measurement device is a photometric detector or spectroradiometer. Different measuring devices can meet different test requirements, and realize the fast measurement of different quantities.

As a technical scheme, the apparatus comprises one or more reflecting mirror. The said reflecting mirror is set in the observation light path and/or the illumination light path, which reduces the working distance and the volume of the apparatus. It should be pointed out that plurality of reflection mirrors can reduce the working distance may also lead to signal loss, and affected the subsequent light detecting. Therefore, the number of mirrors should be selected appropriately, for example, two mirrors can be set in the optical path.

As a technical scheme, the apparatus comprises a monitor device for monitoring the fluctuation of the light source. The monitor device receives the light from the light source. The position of the monitor device can be arranged flexibly, such as can be set at the side of the light source. In this invention, the monitor device can be a spectradiometer or a photoelectric detector or a luminance meter. The quantities which the monitor device obtains can be consistent with the measuring device. As the preferred, the apparatus comprises a case, and the light source, sampling device, color filter, color filter wheel, measuring device, and monitor device are all arranged in the case. With the integration design, it can operate conveniently. There is human-computer interface in the case, for example a display with a touch screen, touch screen control unit and the microprocessor, for intelligent processing and test data, real-time display of test conditions and test results.

In summary, this invention includes a set or more sampling devices, each consists of a holed mirror and a circular aperture, and one or more measurement devices corresponding to the sampling devices. By flexibly selecting the size of circular aperture and the holed mirror, it can be applied to all kinds of observation angle. At the same time, it can be figured with various filters and monitor device flexibly to realize diversification of measurement function. It has the advantages of fast measurement, high accuracy, small volume, wide application range, strong function and design integration, and can be widely applied to laboratory, industrial production line and field fast measurement etc.

DRAWINGS

Figure 2:
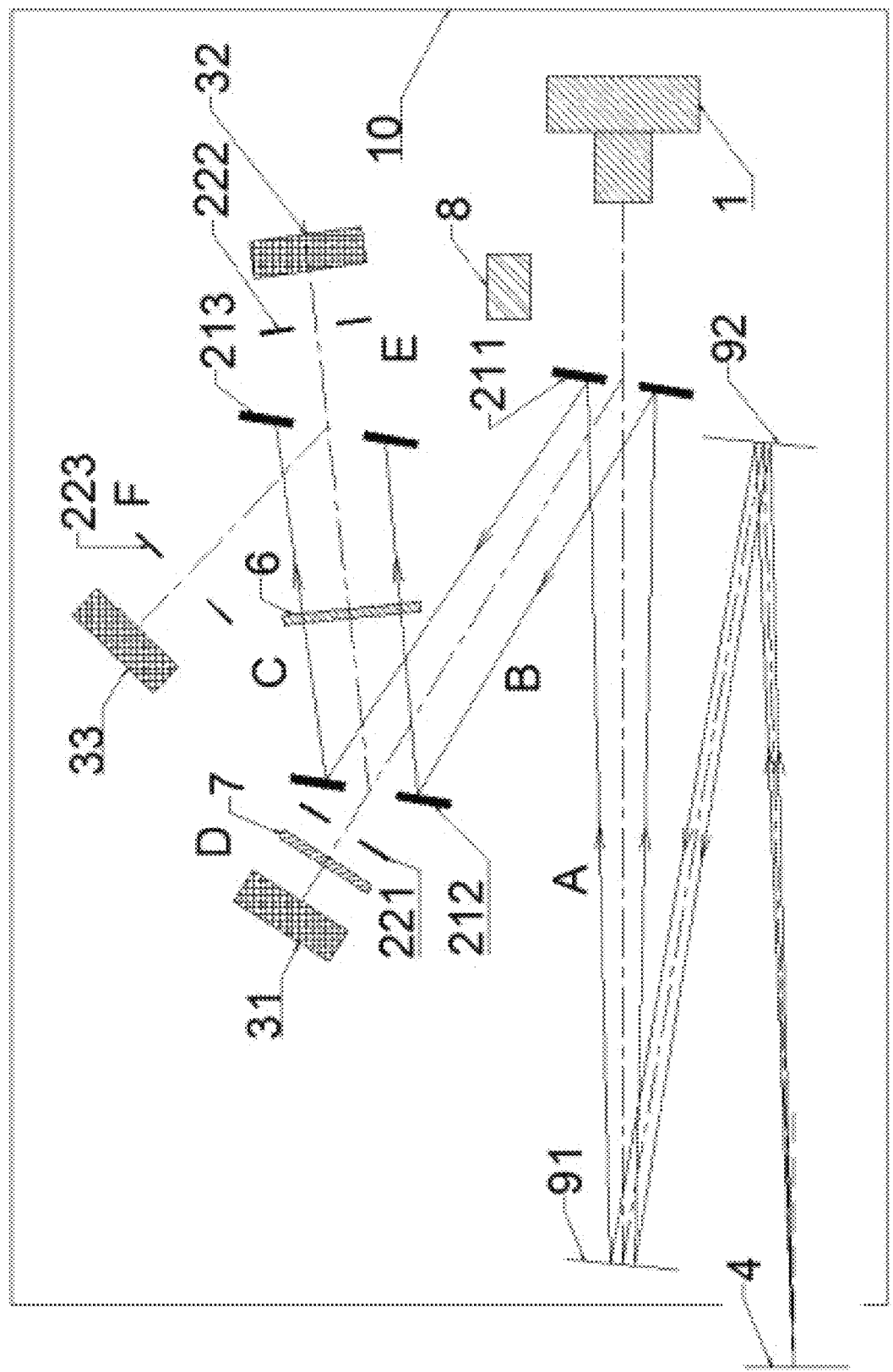
Figure 4:
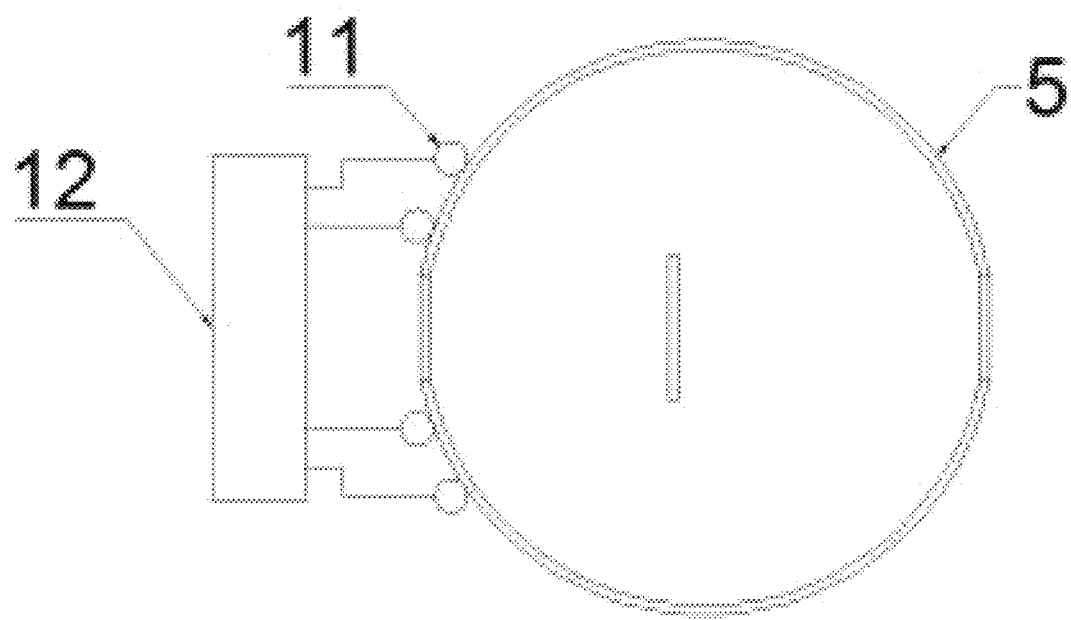

FIG. 1 is a schematic view of embodiment 2;
FIG. 2 is a schematic view of embodiment 3;
FIG. 3 is a schematic view of filter wheel with color filter of the embodiment 3,
FIG. 4 is a light source schematic view of embodiment 4;
1—light source; 211 and 221, 212 and 222, 213 and 223—sampling device; 31, 32, and 33—measuring device; 4—test sample; 5—integrating sphere; 6—color filter; 7—filter wheel; 8—monitoring device; 91 and 92—reflecting mirror; 10—case; 11—color LED; 12—driving device.

DETAILED DESCRIPTION OF THE PREFERRED EMBODIMENT

Embodiment 1

This embodiment realizes single observation angle for retro-reflection measurement. The apparatus comprises a light source, one set of sampling device, one measuring device and a test sample. The sampling device is composed of a holed mirror and a circular aperture. Both centers of the holed mirror and the circular aperture are located in the optical axis of the observation light path. The light source, holed mirror, test sample, the circular aperture and the measuring device are arranged in sequence in the optical path.

The embodiment realizes 0.2° observation angle, which corresponds to 0.2°±0.05° annular band of light. The light emitted by the light source passes through the holed mirror and irradiates to the test sample, and the retro-reflect light from the test sample goes to the holed mirror first, and the light whose beam angle larger than 0.15° was reflected to the circular aperture, and the light whose beam angle smaller than 0.25° passes through the circular aperture, and shapes a 0.2°±0.05° annular band of light, which is finally received by measurement device behind circular aperture to fulfill retro-reflection measurement in 0.2° observation angle.

The optical path in this embodiment is simple and ingenious, without supporting device, and can complete realization of 0.2°±0.05° annular band of retro-reflect light measurement. It has advantages of high measuring accuracy, simple system structure, compact, convenient operation, and fast test speed for producing line and on-site rapid measurement in industry.

Embodiment 2

As shown in FIG. 1, this embodiment comprises one light source 1, three sampling devices (211 and 221, 212 and 222, 213 and 223) and three measuring devices (31, 32, and 33), a monitor device 8, a set of reflecting mirror (91 and 92) and a case 10. The set of reflecting mirror (91 and 92) is set in the light path between the light source 1 and the test sample 4. The light source, sampling devices (211 and 221, 212 and 222, 213 and 223), measuring devices (31, 32, and 33), monitor device 8 and reflecting mirror (91 and 92) are all located in case 10. Different from embodiment 1, there are two reflecting mirrors 91 and 92 in the illumination light path to minimize of the apparatus; In addition, there are three sets of sampling devices (211 and 221, 212 and 222, 213 and 223), it can achieve three annular bands of light for three observation angles' measurement.

Three sets of sampling devices in this embodiment has observation angles: 0.2°, 0.33° and 0.5° which corresponds to the bands of 0.2°±0.05°, 0.33°±0.05° and 0.5°±0.05° respectively. The different measuring annular bands are sequentially arranged from small to large in the observation light path. Along with the observation light path, the holed mirror of later sampling device is in front of circular aperture of former sampling device. This means that the second holed mirror 212 of the second sampling device is in front of the first circular aperture 221 of first sampling device, and the third holed mirror 213 of the third sampling device is in front of the second circular aperture 222 of second sampling device.

The light emitted from the light source 1 passes through the holed mirror 211, and reflected by two reflecting mirrors 91 and 92, and then irradiates to the test sample 4. The retro-reflect light from the test sample 4 goes back to the holed mirror (211), and the light whose beam angle larger than 0.15 is reflected to the next holed mirror (212). One part of the light pass through holed mirror 212 with aperture size of 0.28°, and then sequently cut by a circular aperture 221 with aperture size of 0.25°; the corresponding measuring device 31 receives an annular band)(0.15°~0.25° of light.

The other part of light whose beam angle greater than 0.28° are reflected by the second holed mirror 222 along the observation light path to the third holed mirror 213. One part of the light pass through the third holed mirror 213 with aperture size of 0.45°, the second circular aperture 222 cut the light which beam angle greater than 0.38°, therefore, the second measuring device 32 receives 0.28°~0.38° annular band of light. Another part of the light whose beam angle greater than 0.45° are reflected by third holed mirror 213 along the observation light path to the third circular aperture 223 which cut the light whose beam angle is greater than 0.55°, the third measuring device 33 receives annular band of light in the range from 0.45°~0.55°. The retro-reflection measurement can be realized under the different observation angles at one time. It can greatly reduce the test time and improve test efficiency.

This embodiment also comprises a monitor device 8 arranged at the side of the light source 1 to receive the light emitted from the light source 1. Both the measuring device 3 and the monitor device 8 are spectroradiometer. Make full use of the measured results, it obtains photometric, colorimetric and spectral quantities such as reflectivity, spectral reflectance and light emitting intensity coefficient.

Embodiment 3

As shown in FIG. 2, different from embodiment 2, this embodiment includes a color filter 6, the color filter 6 is set in the common observation light path between the second holed mirror 212 and the third holed mirror 213. Both the second measuring device 32 and the third measuring device 33 are photoprobes. The filter 6 matches the spectral responsivity of the photobrobes to the CIE spectral luminous efficiency function $V(\lambda)$, because the filter is set in the common observation optical path C, the light received by measuring device 32 and measuring device 33 are functioned by filter 6 and photometric value in different observation angle can be obtained.

In addition, this embodiment includes a filter wheel 7, which is arranged between the first circular aperture 221 in first sampling device and the first measuring device 31. As shown in FIG. 4, there are 4 filters 6 in filter wheel 7, the first measuring device 31 is a CCD, the spectral responsivity of three filters combined with the CCD are CIE tristimulus function $x(\lambda)$, $y(\lambda)$ and $z(\lambda)$. The filter wheel under the driving of the driving device can realize retro-reflection tristimulus values measurement. The other combined spectral response is CIE spectral luminous efficiency function $V(\lambda)$, it can get a retro-reflection photometric values under photopic luminance values.

Embodiment 4

Different from the above embodiments, this embodiment comprises an integrating sphere 5. Four color LEDs 11 are set in the wall of the integrating sphere 5, the color LED 11 are connected to a programmable driver 12 which controls each color LED 11 in pulse mode. The light from one or multi color LEDs 12 is mixed in the integrating sphere 5, and then irradiates to sample 4 uniformly, avoiding measurement error introduced by the non-uniformity of the illumination light.

What is claimed is:
1. An apparatus for retro-reflection measurement, comprising:
a light source, one or more sets of sampling devices for annular measurement, and one or more measurement devices corresponding to the sampling devices;

wherein one set of the sampling devices consists of a holed mirror and an circular aperture; the illumination light path is the light from said light source going to a test sample at a certain entrance angle, and the observation light path is retro-reflected light from the test sample passing through the holed mirror and the circular aperture to form an annular band which meets an observation angle condition and is then received by a corresponding measurement device optically downstream of one of the sets of sampling devices, the observation angle condition defined by an optical path that allows the retro-reflected light to transmit through the holed mirror and through the circular aperture to be received by the corresponding optically downstream measurement device.

2. The apparatus for retro-reflection measurement according to claim 1, wherein the diameter of the open hole in the holed mirror is less than the diameter of the circular aperture, and the combination of the holed mirror and the circular aperture are configured to shape an annular band of light such that the holed mirror reflects the light that is outside of the inner diameter while the circular aperture cuts the light that is outside of the external diameter of the annular band.

3. The apparatus for retro-reflection measurement according to claim 1, wherein the center of the holed mirror and the center of the circular aperture are located in an optical axis of the observation light path.

4. The apparatus for retro-reflection measurement according to claim 1, wherein, there are two or more sets of sampling devices; and along the observation light path, the holed mirror of the sampling device in the downstream of the observation light path is in front of the circular aperture of the sampling device in the upstream of the observation light path.

5. The apparatus for retro-reflection measurement according to claim 1, wherein the annular bands shaped by the multiple sets of sampling devices are sequentially arranged from small to large in the observation light path.

6. The apparatus for retro-reflection measurement according to claim 5, wherein the observation angle of the annular bands are 0.2°, 0.33° or 0.5°, the observation angle allowing the retro-reflected light to transmit through the holed mirror and through the circular aperture to be received at the measurement device corresponding the set of sampling device.

7. The apparatus for retro-reflection measurement according to claim 1, wherein said light source comprises one or more programmable LEDs of different color; said LEDs emit light independently or with combination, and the light goes to the test sample directly or indirectly.

8. The apparatus for retro-reflection measurement according to claim 7, wherein the LEDs are driven in pulse mode.

9. The apparatus for retro-reflection measurement according to claim 7, further comprising an integrating sphere, wherein the light emitted for one or more LEDs independently or with combination goes into the integrating sphere and then irradiates to the test sample.

10. The apparatus for retro-reflection measurement according to claim 1, further comprising one or more color filters set in the observation light path and/or the illumination light path.

11. The apparatus for retro-reflection measurement according to claim 10, further comprising a color filter wheel with one or more color filters; a color filter is switched into the light path by rotating the color filter wheel.

12. The apparatus for retro-reflection measurement according to claim 10, wherein the observation light path includes a common observation light path of the two or more measuring annular band and an independent observation light path corresponding to each individual measuring annular band; the said color filter is set in the common observation light path or the independent observation light path.

13. The apparatus for retro-reflection measurement according to claim 1, further comprising a monitor device for monitoring fluctuation of the light source; said monitor device receives the light from the light source.

14. The apparatus for retro-reflection measurement according to claim 1, further comprising one or more reflecting mirrors; said reflecting mirror is set in the observation light path and/or the illumination light path.

15. The apparatus for retro-reflection measurement according to claim 1, wherein said measurement device is a photometer detector or a spectroradiometer.

* * * * *